United States Patent [19]

Groshong et al.

[11] Patent Number: 4,549,879

[45] Date of Patent: Oct. 29, 1985

[54] VALVED TWO-WAY CATHETER

[75] Inventors: LeRoy E. Groshong; Ronald J. Brawn, both of Portland, Oreg.

[73] Assignee: Catheter Technology Corporation, Salt Lake City, Utah

[21] Appl. No.: 491,258

[22] Filed: May 3, 1983

[51] Int. Cl.$^4$ ............................................. A61M 25/00
[52] U.S. Cl. .......................................... 604/247; 604/9
[58] Field of Search ............... 604/247, 280, 256, 170, 604/8–10; 137/493, 848

[56] References Cited

U.S. PATENT DOCUMENTS

| | | | |
|---|---|---|---|
| 2,393,003 | 1/1946 | Smith | 604/170 |
| 3,020,913 | 2/1962 | Heyer | 604/247 X |
| 3,128,769 | 4/1964 | Scislowicz | 604/170 |
| 3,885,561 | 5/1975 | Cami | 604/247 |
| 4,434,810 | 3/1984 | Atkinson | 137/493 |
| 4,475,898 | 10/1984 | Brodner et al. | 604/9 |

Primary Examiner—Dalton L. Truluck
Attorney, Agent, or Firm—Klarquist, Sparkman, Campbell, Leigh & Whinston

[57] ABSTRACT

Catheter of soft, flexible material is formed with closed end. Fluid opening formed by single slit through tubing wall of such length that valve will open only upon application of predetermined pressure differentials. Removable stiffener member is positioned in catheter, abutting closed end to push catheter into body vessel when inserting.

2 Claims, 6 Drawing Figures

VALVED TWO-WAY CATHETER

BACKGROUND OF THE INVENTION

The invention relates to a two-way valved vascular catheter fabricated of extremely soft, flexible material and utilizing a removable internal pushing member abutting the closed proximal end to allow intravascular insertion. The two-way valve permits fluid to flow from the catheter if a predetermined pressure differential between inside and outside the catheter is exceeded but prevents flow in the opposite direction unless a second predetermined negative pressure differential is exceeded.

Our U.S. Pat. No. 4,327,722, entitled Method for Intravenous Therapy and Hyperalimentation, disclosed a flexible silicon rubber catheter which has a slit valve adjacent its closed proximal end. The term "proximal end" refers to the forward end of the catheter which is inserted into the patient's body. The term "distal end" refers to the rearward end thereof which is situated externally of a patient's body.

The valved catheter disclosed in such patent was designed for hyperalimentation, in which high concentrations of nutrients are infused into the venous system, as well as other instances in which therapeutic agents or the like are intravascularly administered. The catheter valve of such catheter was designed to prevent retrograde flow of blood into the proximal end of the catheter. When the hydrostatic pressure inside the catheter exceeds the pressure outside the catheter by a predetermined amount, the potential opening defined by the valve slit expands to allow fluid to flow undirectionally through and out of the catheter. When the pressure differential drops below this predetermined amount, the valve opening closes to prevent retrograde flow of blood into the catheter.

One prior art catheter having a slit defined one-way valve is the PUDENZ (trademark) atriocephalic catheter manufactured by Heyer-Schulte, Inc., a subsidiary of American Hospital Supply Export Corporation. This catheter of silicon rubber is specifically designed to drain ventricular fluid from the brain to the heart to relieve excess ventricular pressure. It is formed with a closed end and with four equiangularly positioned slits adjacent the end. Because of its design, fluid could flow only out of the slits. The valved end of the catheter is disposed within the right atrium of the heart, thus preventing the retrograde flow of blood from the heart into the cerebral ventricles. While this is the primary designed use of the PUDENZ atriocephalic catheter, it has also occasionally been used to infuse therapeutic fluids into the vascular system.

Another slit valved one-way catheter of silicon rubber, formerly marketed by the Extracorporeal Company, was used for intravascular infusion. The Extracorporeal catheter had a slit valve which, due primarily to the short slit length, was adapted only to permit fluid flow out of the catheter.

We realize that it would be desirable and advantageous to modify the valve of our previously disclosed closed ended intravascular infusion catheter so that retrograde flow from the blood vessel through the catheter valve would be possible under certain defined conditions. Such a valved catheter could not only be used to infuse fluids into the body but also to withdraw blood or other body fluids for analysis, to relieve excess pressure, as well as to permit confirmation of the catheter's position during insertion.

U.S. Pat. No. 3,885,561 to Cami discloses a closed ended catheter for the administration of epidural anesthesia. The illustrated catheter has a plurality of longitudinal slits through which fluid can escape from the catheter but through which body fluid can be drawn, it is stated, upon the application of negative pressure in the catheter. So that the catheter wall will not collapse, the slits are longitudinally and circumferentially offset from one another so that no single diametral plane has more than one slit and the dihedral angle between the diametral planes carrying adjacent slits is at least 45°.

Notwithstanding the possible utility of such a catheter for the administration of epidural anesthesia, its use in other areas of medical therapy, and specifically in the area of extended intravascular therapy and access, is associated with several serious drawbacks.

First, the Cami catheter is fabricated of a thermoplastic material, and it must be of sufficient rigidity and stiffness that it can be easily advanced through an introducing needle and into the tissues without bending or kinking which would obstruct the flow of anesthetic fluid through the catheter or resist withdrawal of fluid from the catheter.

The use of stiff, thermoplastic material is disadvantageous for catheters adapted for extended intravascular implantation. A stiff catheter will not conform to the curvature of vessels and thus will impinge on the luminal surface of vessels into which it is placed, especially at points of curvature, causing irritation and erosion of the vessel lining endothelium. This reaction, in blood vessels, will lead to inflammation of the endothelium with an increased tendency for local clot formation and thrombosis. An additional disadvantage is that with a stiff, nonstretchable catheter, relative motion between the skin insertion site and the point of catheter attachment to the skin such as occurs during repeated movement, for example, during respiration or voluntary muscular movement of the arm or hand, will cause the catheter slightly to move in and out through the epidermal penetration site and thus introduce bacteria on the skin surface into the insertion wound and along the catheter surface. This may result in infection at the insertion site which may extend along the catheter into the vessel in which the catheter is implanted. Septicemia may result. A further disadvantage is that the stiff catheter material may kink to obstruct flow of therapeutic fluid therethrough or impair withdrawal of body fluids. This is especially likely if the catheter is placed across a joint space, where repeated flexion and extension occurs. Thus, such catheter is restricted in its anatomical areas of usage.

It will be appreciated that the disadvantages of a stiff, thermoplastic fabrication material are of much greater medical consequence if the catheter must be in place and maintain function without complications for days, weeks, months, or even years as is the case for intravascular catheters.

Moreover, a catheter of a thin, relatively stiff plastic material is subject to fracture contiguous the valve opening upon repeated cycles of valve opening.

Another serious drawback of a valved catheter of stiff material is the damage caused to cellular elements which are injected into the body or withdrawn from the body through the valves of the catheter. With a stiff thermoplastic material, significant pressure differential between inside and outside the catheter is necessary to cause the valve to open in either direction. The cellular elements such as erythrocytes, leukocytes, or platelets which are infused through the catheter valve are subjected to forces and pressure differentials which may damage or destroy them. This would cause hemolysis of erythrocytes and functional damage to other cellular elements such that after forcible injection they no longer maintain their normal function. This could be an even greater problem when body fluids containing cellular elements are withdrawn through a valve in a stiff catheter. Because significant negative pressure must be applied to cause the valve to open, cells drawn through the valve are subjected to a dramatic pressure change which could result in cell rupture and damage. Chemical or hematologic analysis performed on body fluid withdrawn through such a valve may not be accurate due to such damage, and errors in subsequent patient therapy would result.

Yet another disadvantage of a slit valve in the wall of a stiff catheter is that the valve surfaces, being fabricated of a stiff plastic material, will tend to lose their ability to form absolutely tight seals after several cycles of usage. That is, each cycle of deformity inward and outward causes the stiff, inelastic surfaces to move against each other and may result in permanent deformities in the surfaces, especially at the sharp internal and external edge of the valve surface. If such occur, they allow inadvertent retrograde flow into the catheter lumen with its attendant adverse effects of clot formation within the catheter, rendering it unusable, or possible retrograde hemorrhage through the catheter should it become distally disconnected.

SUMMARY OF THE INVENTION

The present invention responds to the above needs by providing a closed ended catheter fabricated of a soft, extremely flexible, biocompatible material and having a removable internal pushing member abutting the closed end and a simply fabricated, long-lived two-way valve adjacent the closed proximal end. The removable internal pushing member allows the extremely soft, flexible catheter easily to be drawn into a vessel by pushing the member against the proximal closed end. The two-way valve consists of a single linearly extending slit means which focally weakens the catheter wall adjacent the closed end. The slit valve remains closed under normal physiologic pressures but allows the catheter wall contiguous the slit to deform when sufficient pressure gradients are applied across it such that the slit valve surfaces are not in direct opposition and thus allow an orifice through which fluid may flow out of the catheter or be drawn into the catheter.

It is a primary object of the present invention to provide a two-way valved catheter fabricated of an extremely soft, flexible, biocompatible material such that trauma to a body vessel due to insertion and prolonged intravasular placement is reduced and complications such as inflammation, thrombosis, and septic vasculitis are obviated. Another object of the present invention is to provide a flexible two-way valved catheter which may be introduced and advanced through vessels utilizing a removable internal pushing member abutting the closed proximal end of the catheter. Thus, exceedingly soft and flexible valved catheters may be introduced into and advanced through vessels by means of the removable internal member pushing against the closed proximal catheter end and pulling the catheter into position by pressure against the closed end.

It is a further object of the present invention to provide a two-way valved catheter which may be placed in vessels crossing joint spaces or other positions in which repeated flexion, extension, or twisting motions may occur without the risk of catheter failure due to catheter kinking or fracture. An additional object is to provide a catheter which does not permanently kink and which, when bent, has elastic memory characteristics which allow it to retain its previous form without permanent kinking or deformation. It is a further object to provide a two-way valved catheter which is strong and stretchable to resist sliding in and out of the skin insertion site due to repetitive voluntary or involuntary movements such that skin bacteria are not continuously being drawn beneath the skin at the catheter insertion site. It is also an objective to provide a catheter of a stretchable material which will resist dislodgement if accidentally pulled upon.

It is another object of the present invention to provide a two-way catheter valve which prevents retrograde flow of blood into the catheter under normal physiologic conditions, thus preventing blood accumulation in the proximal end of the catheter which may result in clot formation within the catheter lumen such as to interfere with and stop the flow of fluid therethrough. This would render the catheter inoperative and necessitate its withdrawal. It is a further object to prevent the possibility of hemorrhage through the catheter should the distal end become accidentally disconnected. It is a further objective of the present invention to provide a two-way valved catheter which permits the measurement of venous pressure without requiring intricate sensing and measuring devices and without requiring that blood flow in a retrograde manner into the proximal end of the catheter. It is yet another object to provide a two-way valved catheter with sufficient resistance to valve opening that the venturi effect of blood flowing through a vessel in which the catheter is disposed will not cause the catheter valve to open, thus reducing the likelihood that air could enter the blood stream through the catheter in the event that the distal end of the catheter becomes inadvertently disconnected. This may prevent the occurrence of catastrophic air embolism.

It is a further object of the present invention to provide a two-way catheter valve fabricated of extremely pliable, flexible material such that the valve is resistant to fracture and failure during innumerable repetitive cycles of opening and closing in antegrade and retrograde directions and for extended periods of implantation. It is another object to provide a valve fabricated of soft elastic material such that permanent deformity of the valve surfaces does not occur with repeated valve use and thus that valve leakage and failure due to damage of the valve faces and edges is eliminated. A further object is to provide a valve with good elastic memory such that after a pressure differential causes deformation of the catheter contiguous the valve to cause the valve surfaces to separate, forming a temporary orifice through which fluid may be infused or withdrawn, cessation of the pressure gradient will result in the catheter wall immediately assuming its resting configuration with the valve immediately closing so as to prevent any reflux of blood or body fluid into the catheter lumen.

It is a further object of the present invention to provide a two-way catheter valve which is fabricated of soft, pliable, biocompatible material and operated by low differential pressures such that withdrawal or injection of cellular elements through the catheter valve will not substantially damage, rupture, or change the physiologic activity of the cells. Another object is to provide a catheter valve through which biologic fluids can be drawn without affecting or changing their chemical or hematologic characteristics.

It is a final object of the present invention to provide a two-way catheter valve which is exceedingly simple in its fabrication and which, because of its simplicity, will function for extended periods of time without failure.

BRIEF DESCRIPTION OF THE DRAWINGS

The invention will be better understood and further objects will become apparent when consideration is given to the following detailed description thereof. Such description makes reference to the annexed drawings wherein.

DETAILED DESCRIPTION OF THE PREFERRED EMBODIMENTS

Figure 1:
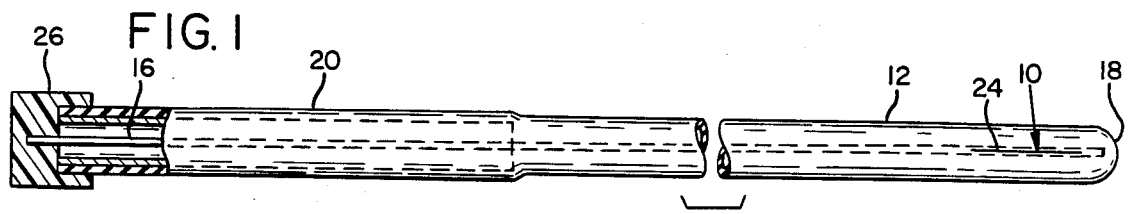
FIG. 1 is a schematic side elevation view of a catheter incorporating an embodiment of the two-way valve, proximal closed end, and distal internal bushing.
Figure 2:
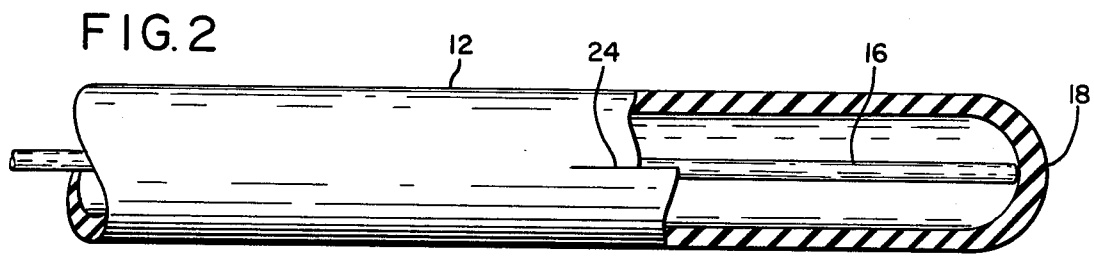
FIG. 2 is a view of the proximal end of the catheter of the invention partially broken away and showing the removable internal stiffening member abutting the closed end of the catheter.
Figure 3:
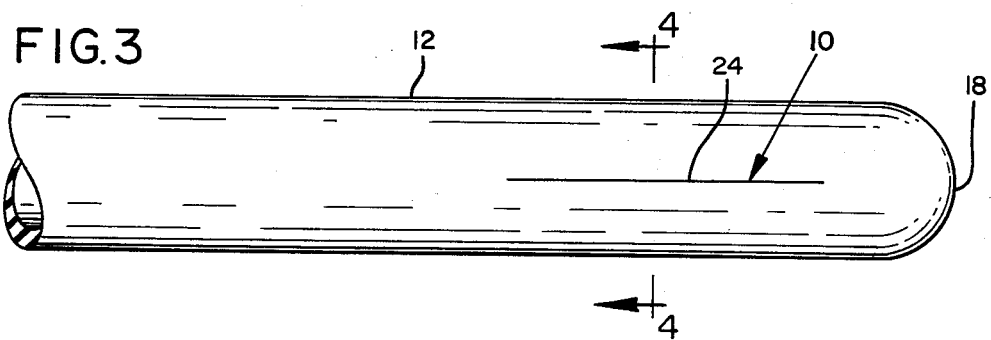
FIG. 3 is an enlarged fragmentary side elevation view of the proximal end of a catheter which incorporates an embodiment of the two-way valve.

The principles of this invention are particularly useful when embodied in a two-way valved catheter such as that illustrated in FIGS. 1 through 4, the valve being generally identified with the number 10. The valve 10 is typically disposed in a catheter 12 fabricated of a durable, flexible, biocompatible material such as silicon rubber. Typically, such catheter material should have a hardness of less than 100 durometer and an elongation percentage of up to 700. A preferred material is a silicon rubber tubing having a hardness of about 59 durometer sold under the trademark SILASTIC by Dow Corning Co., Midland, Mich. The catheter 12 is preferably partially translucent so that the physician can determine the presence of air bubbles or blood therein. The proximal end 18 of the catheter 12 is closed and preferably symmetrically rounded. The distal end may include an internal bushing 20 which is provided so that an adaptor, not shown, for connecting the catheter to a source of fluid may be fixed onto the distal end.

The catheter 12 has a relatively small outside diameter so that it can be readily inserted into a vessel, such as the subclavian vein, without causing undue trauma to the vessel and the surrounding tissue. Typically, this requires the catheter have an outside diameter not exceeding 0.125" (0.318 cm). The inside diameter of the catheter must be sufficiently large as to permit solution to flow therethrough at a rate sufficient to allow the required amount of nutrient or therapeutic agent to be administered. Examples of suitable catheters are those with an outer diameter of 0.089" (0.226 cm) and an inner diameter of 0.052" (0.132 cm); an outer diameter of 0.069" (0.175 cm) and an inner diameter of 0.045" (0.114 cm); and an outer diameter of 0.060" (0.152 cm) and an inner diameter of 0.040" (0.102 cm). Catheters with smaller inner and outer diameters may also be used.

Due to the soft, pliable nature of the material from which it is fabricated, to insert the catheter it is essential to utilize a removable internal pushing member 16 which abuts the closed end 18 of the catheter 12. A force directed against the internal pushing member 16 causes its proximal end to push against the closed proximal end of the catheter 12 causing the catheter to be drawn forward from its proximal closed end. This allows the catheter easily to be advanced into and through blood vessels or other body spaces. The distal end of the pushing member 16 preferably is fixed to an end cap 26 which fits over the distal end of the catheter 12 as shown in FIG. 1 with the proximal end of the pushing member in abutment and approximation with the closed proximal end of the catheter throughout any insertion manipulation. This helps prevent inadvertent penetration of the catheter end 18 with the pushing member.

The catheter 12 may be used for either short-term or long-term intravascular therapy, hyperalimentation, or vascular access. It may also be used for other purposes such as relieving excess pressure or treatment of other nonvascular problems. Other applications of the invention will be evident to those skilled in this art. However, this discussion has and will continue to deal primarily with vascular applications. Regardless of the particular application, the catheter 12 should be long enough to extend from the site of insertion to a suitable vessel which is sufficiently large that it will not be adversely affected by such therapy.

The catheter may have external and internal coatings of an anticoagulant substance such as TDMAC Heparin to prevent the formation of blood clots thereon. However, the design of the catheter 12 is such that the presence of anticoagulants is not critical.

The two-way valve 10 in the catheter 12 is formed by a single linearly extending slit 24 cut through the catheter wall adjacent the proximal end 18. This focally weakens the catheter wall so that upon the application of a sufficient pressure differential internally and externally of the catheter, the catheter wall in the vicinity of the valve will deform such that the two valve surfaces are not in complete contact and thus form an orifice through which fluid may pass out of or into the catheter. Thus, as shown in FIG. 4b, the valve 10 opens outwardly when the fluid pressure inside the catheter is greater than the fluid pressure outside the catheter by a predetermined amount. The application of suction or vacuum pressure to the catheter lumen will cause the pressure outside the catheter to exceed the internal pressure. As shown in FIG. 4c, when this differential exceeds a predetermined amount, the catheter wall in the area of the valve 10 will partially or completely collapse such that the valve surfaces are not in complete contact and thus allow an orifice to form through which retrograde withdrawal of fluid through the catheter may be accomplished.

Figure 4A:
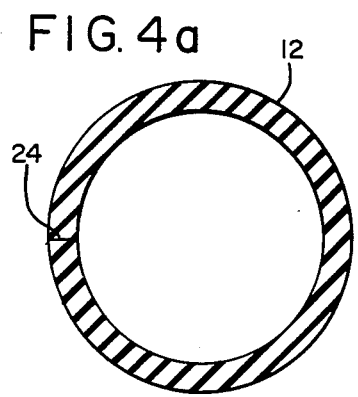
FIG. 4a is an enlarged sectional view taken along line 4—4 of FIG. 3 showing the two-way valve in the normal closed position.
Figure 4B:
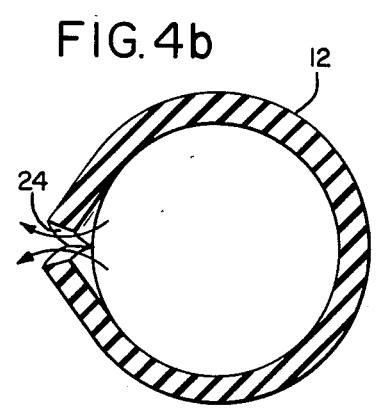
FIG. 4b is an enlarged sectional view taken along line 4—4 of FIG. 3 showing the two-way valve in an opened condition, permitting fluid to flow through the valve and out of the catheter.
Figure 4C:
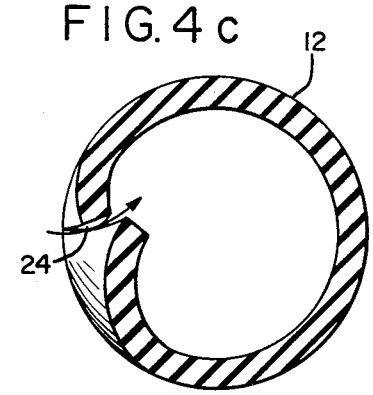
FIG. 4c is an enlarged sectional view taken along line 4—4 of FIG. 3 showing the two-way valve in an opened condition with fluid being drawn retrograde through the valve and into the catheter.

It is desired that under normal physiologic conditions the catheter valve remains closed as demonstrated in FIG. 4a. Thus, in the event that the distal end 20 of the catheter 12 becomes disconnected, atmospheric pressure will not cause air to pass from the catheter through the valve and into the blood stream, nor will it back bleed. Likewise, the venturi effect of blood flowing past the proximal valved end of the catheter will not be sufficient to cause air to be drawn from the catheter into the blood stream.

It is highly desirable that the catheter 12 be treated in the vicinity of the valve 10, and preferably on the valve faces, by a biocompatible chemical which will focally weaken and make more pliable the catheter material such that the treated portion is more easily deformable upon the application of pressure gradients across the catheter wall, thus facilitating catheter valve function. One suitable agent is a dimethylsiloxane containing material sold by Dow Corning Co. under the designation Dow Corning Fluid 360. By applying said chemical to the valve surfaces as well as the surrounding internal and external catheter walls for at least one minute, sufficient dimethylsiloxane is adsorbed into the silicon catheter wall focally to weaken the catheter wall contiguous the valve for an extended period of time. This renders the treated portion of the catheter more pliable such that it is more easily deformed by the application of pressure gradients across the catheter wall. That is, after treatment with the chemical the valve will open to allow outward flow of fluid through the catheter at a lesser pressure gradient than if the valve and surrounding catheter wall had not been treated. Likewise, a lesser negative or suction pressure is necessary to cause the catheter wall to collapse such that the valve surfaces are no longer in complete contact and thus allow an orifice through which fluid may be withdrawn into the catheter. Thus, the essential valve function of the two-way valved catheter is facilitated; the potential for damaging erythrocytes or other formed cellular elements infused through or withdrawn through the valve is decreased; and the longevity of the valve is increased. By way of example, with a SILASTIC tube of 0.052 inch internal diameter and 0.089 inch outer diameter with a valve of 0.125 inch in length of which the valve surfaces and the contiguous catheter wall have been immersed for five minutes in polydimethylsiloxane liquid having a viscosity of 100 cs at 25° C., resulting in the opening of the slit valve upon the application of eleven inches mercury negative pressure and upon the application of six inches water positive pressure. In a similar tube with a slit length of 0.250" the slit opened upon the application of 9.5 inches mercury negative pressure and upon the application of 2.875 inches water positive pressure.

With various tube materials and sizes the desired slit length necessary can be determined by experimentation. We have found it desirable to provide a slit that will open upon the application of negative pressure between three to twenty inches mercury. This will provide a slit that will open at reasonable positive pressures to permit fluid to pass from the catheter but at the same time will prevent accidental opening such as has been described above.

PLACEMENT AND OPERATION OF THE TWO-WAY VALVED CATHETER

As mentioned above, the catheter 12 is suited for either temporary or permanent implantation in either central or peripheral vascular applications. When used for temporary or permanent central vascular applications, such as hyperalimentation, the method and apparatus disclosed in our U.S. Pat. No. 4,327,722 is suitable for directing the catheter into the body and through the appropriate vessels. The utility and necessity of utilizing an internal pushing member abutting the closed proximal end of the catheter so as to draw the soft, pliable catheter into the blood vessel by pressure exerted against the closed catheter end has previously been described.

An advantage of the two-way valved catheter is that during insertion into the vascular system the physician may periodically withdraw blood through the catheter valve to ensure that the proximal end of the catheter remains in the blood vessel. This was not possible with the previously described one-way valved SILASTIC catheters.

Once the catheter 12 is installed in the appropriate vascular or other channel, therapeutic or nutritive fluid may be pumped into the body through said valve 10. However, until the pressure in the catheter 12 is deliberately raised by the physician or attending medical personnel to a point which causes the valve to open, the valve will remain closed and thus prevent air from entering the body through the catheter as well as preventing flow of blood or other fluids from the body into the catheter. This prevents hemorrhage or the like which could result if the valve were not present to prevent retrograde flow into the catheter. Likewise, it prevents the subsequent formation of blood clots within the catheter lumen which would impede or completely block further flow of fluid, in either direction, through the catheter. The natural venturi effect of blood within the vascular system will not be sufficient to cause the valve to open.

When fluid is to be administered, the physician raises the fluid pressure within the catheter by suitable pump or syringe means, or by raising a container of intravenous fluid, nutrient, or therapeutic solution to sufficient height that the hydrostatic pressure head will exceed the opening pressure of the valve, approximately 8 inches of water, thereby outwardly deforming the catheter wall adjacent the slit valve and opening the slit to permit fluid to flow through it and into the system as depicted in FIG. 4b.

To determine the central venous pressure of the patient in whom the catheter is disposed the container of fluid may be raised or lowered until the fluid flow first starts or stops. Alternatively, fluid may be bled into a manometric tube and allowed to reach equilibrium. The hydrostatic pressure defined by the bottle height or manometer is measured; the predetermined opening pressure of the valve is subtracted; and the central venous pressure easily calculated by untrained medical personnel without using complex, expensive, and potentially troublesome sensing and measuring devices and without allowing retrograde flow of blood into the proximal catheter lumen with the concomitant risk of clot formation in the catheter. It is possible, utilizing this method, continuously to monitor central venous pressure without risk of catheter failure.

When the bottle of intravenous fluid is empty and there is no longer a sufficient pressure head to keep the valve open, it will automatically and reliably close. Thus, the risk of air embolism is virtually eliminated. Likewise, the risk or retrograde blood flow into the catheter occurring when the fluid source runs dry is eliminated.

If a blood sample is to be withdrawn from a vein or other vessel, suction is drawn on the catheter such as by means of a syringe. Once a sufficient vacuum pressure is drawn, the catheter wall adjacent the valve, chemically treated as previously described, will deform or collapse such that the valve surfaces are not in exact apposition to each other, thus forming an orifice through which fluid may be withdrawn with ease. By way of example, with a SILASTIC tube of 0.052 inch internal diameter and 0.089 inch outer diameter with a valve of 0.125 inch in length of which the valve surfaces and the contiguous catheter wall have been immersed for five minutes in polydimethylsiloxane liquid having a viscosity of 100 cs at 25° C., resulting in the opening of the slit valve upon the application of eleven inches mercury negative pressure and upon the application of six inches water positive pressure. In a similar tube with a slit length of 0.250" the slit opened upon the application of 9.5 inches mercury negative pressure and upon the application of 2.875 inches water positive pressure. This will occur as depicted in FIG. 4c. It may be desirable, under some circumstances, to provide a so-called bump to facilitate withdrawal of fluid into the catheter. This is, however, up to the discretion of the physician. The "bump" means to rapidly draw a sufficient negative pressure that the catheter contiguous the valve is completely collapsed. In this configuration no fluid may be withdrawn through the catheter valve. However, as suction is released, the catheter wall will begin to assume a cylindrical configuration; and during this change in configuration, the valve surfaces will become separated so as to allow an orifice through which fluid may easily be drawn.

The catheter 12 and its valve 10 may be maintained in the closed position in the body for extended periods of time without resulting in clotting around the valves. This is true whether or not an anticoagulant is provided. It is not necessary to have continuous flow of fluid through the catheter to prevent clot formation within the proximal catheter lumen nor is it necessary periodically to flush out the catheter with anticoagulant. The clotting of blood, of course, might not only impede the subsequent flow of intravenous solution through the catheter but could also serve as a nidus for bacterial growth leading to septicemia.

Of course, it should be understood that various changes and modifications of the preferred embodiments described herein will be apparent to those skilled in the art. Such changes and modifications can be made without departing from the spirit and scope of the present invention and without diminishing its advantages. It is therefore intended that such changes and modifications be covered by the following claims.

We claim:

1. A closed ended tubular catheter of silicon rubber of less than 100 durometer hardness, and a two-way valve in the side wall of said catheter, said valve consisting of a single, normally closed, linearly extending slit extending through the catheter wall, said slit having such length that when predetermined pressure differentials within and without the catheter exist, the catheter wall contiguous the slit deforms and causes the opposed faces of the slit to withdraw from one another and form a temporary orifice through which fluid may be infused or withdrawn the valve area and contiguous catheter wall having been treated with dimethylsiloxane so as to weaken and make more pliable the treated catheter wall in order to facilitate the two-way valve function.

2. A closed ended tubular catheter of silicon rubber of about 59 durometer hardness, and a two-way valve in the side wall of said catheter, said valve consisting of a single, normally closed, linearly extending slit extending through the catheter wall, said slit having such length that when predetermined pressure differentials within and without the catheter exist, the catheter wall contiguous the slit deforms and causes the opposed faces of the slit to withdraw from one another and form a temporary orifice through which fluid may be infused or withdrawn, said catheter having an outer diameter of 0.089 inch, an inner diameter of 0.052 inch, said slit has a length of 0.250 inch and the valve faces and catheter wall surrounding the valve having been immersed in dimethylsiloxane for about five minutes.

* * * * *